US00PP35046P2

(12) United States Plant Patent
Fazio et al.

(10) Patent No.: US PP35,046 P2
(45) Date of Patent: Mar. 21, 2023

(54) APPLE TREE ROOTSTOCK NAMED 'G.484'

(50) Latin Name: ***Malus domestica* x *Malus robusta* hybrid**
Varietal Denomination: 'G.484'

(71) Applicants: Cornell University, Ithaca, NY (US); The United States of America, as Represented by the Secretary of Agriculture, Washington, DC (US)

(72) Inventors: Gennaro Fazio, Geneva, NY (US); Terence Lee Robinson, Geneva, NY (US); Herbert Sanders Aldwinckle, Geneva, NY (US); James Cummins, Alcoa, TN (US)

(73) Assignees: Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/589,324

(22) Filed: Jan. 31, 2022

(51) Int. Cl.
*A01H 5/08* (2018.01)
*A01H 6/74* (2018.01)

(52) U.S. Cl.
USPC ..... Plt./174
CPC ..... *A01H 6/7418* (2018.05)

(58) Field of Classification Search
USPC ..... Plt./174
CPC ..... D01H 5/0875
See application file for complete search history.

(56) References Cited

U.S. PATENT DOCUMENTS

| | | | |
|---|---|---|---|
| PP7,197 | P | 3/1990 | Luby et al. |
| PP22,228 | P3 | 11/2011 | Brown et al. |
| PP23,337 | P3 | 1/2013 | Cummins et al. |
| PP24,073 | P3 | 12/2013 | Cummins et al. |

OTHER PUBLICATIONS

Mazzola, (1998). "Elucidation of the microbial complex having a causal role in the development of apple replant disease in Washington," Phytopathology, 88(9):930-938.
Unpublished U.S. Appl. No. 17/589,341, filed Jan. 31, 2022 titled "Apple Tree Rootstock Named 'G.66',".
Unpublished U.S. Appl. No. 17/589,353, filed Jan. 31, 2022 titled "Apple Tree Rootstock Named 'G.257',".

*Primary Examiner* — Kent L Bell
(74) *Attorney, Agent, or Firm* — Morrison & Foerster LLP

(57) ABSTRACT

A new and distinct variety of apple tree rootstock *Malus* hybrid 'G.484' is described herein. The new variety is a dwarfing, precocious and productive rootstock that is resistant to fire blight (*Erwinia amylovora*) and crown rot (*Phytophthora cactorum*). The 'G.484' rootstock is useful in that it can be propagated clonally and used as a rootstock or root system for apple trees as well as for interstems of apple trees.

7 Drawing Sheets

STATEMENT REGARDING FEDERAL FUNDING

This invention was made with United States government support under a United States Department of Agriculture—Agricultural Research Station Cooperative Research and Development Agreement, Sponsor's Contract Number 58-3K95-M-1031. The government has certain rights in the invention.

Genus and species: *Malus domestica* x *Malus robusta* hybrid.

Variety denomination: 'G.484'.

BACKGROUND OF THE INVENTION

I. Field & Utility Summary

The invention described herein is a new variety of apple tree rootstock. This new apple tree is useful as it can be propagated clonally and used as a root system or interstem for apple trees. This new variety is a dwarfing rootstock that is resistant to fire blight and crown rot. It promotes early bearing to grafted scions, it is productive as a rootstock or interstem of apple trees.

II. Cultivation Summary

'G.484' originated from a planned cross in 1984 in Geneva, N.Y.

SUMMARY OF THE INVENTION

The present invention relates to a new and distinct variety of apple tree rootstock named 'G.484'. The 'G.484' apple tree rootstock is a dwarfing rootstock that is resistant to fire blight (*Erwinia amylovora*), crown rot (*Phytophthora cactorum*) and tolerant to the replant disease complex. The 'G.484' rootstock is useful in that it can be propagated clonally and used as a rootstock or root system for apple trees as well as for interstems of apple trees. 'G.484' is a hybrid from a cross between breeding line '722506-004' (Not patented) and breeding line '74R5M9-823'(Not patented) and is distinct from its parent cultivars in terms of dwarfing and disease resistance combined. The apple tree rootstock 'G.484' produces grafted trees that are 30 to 45 percent of own rooted standard apple trees, it induces good precocity on the scion, it displays high productivity in multiple environments.

I. Breeding History

In the spring of 1984, pollen from *Malus robusta* hybrid '74R5M9-823' apple tree was applied to emasculated flowers of a *Malus domestica* hybrid '722506-004' in Geneva, N.Y. In the fall of 1984, seeds resulting from this pollination were extracted from mature fruit derived from this cross. In the winter of 1984-1985, the seeds were stratified and planted in large flats under conditions effective to germinate seeds and obtain seedlings. When germinated seedlings were about 2.5 cm tall they were inoculated with a mixture of isolates of the oomycete *Phytophthora cactorum* (the causal agent of crown, root rots and contributing factor of the replant disease complex). The flats were flooded to mid-hypocotyl level and kept at 23° C. for one week. Surviving seedlings were transplanted into individual pots.

In the summer of 1985, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #004 was one of the survivors of this battery of inoculations from the same cross and was eventually named 'G.484'. All the surviving plants were transplanted to a nursery field (Geneva, N.Y.) in the fall of 1985 and allowed to grow side shoots for propagation/evaluation. In the period between 1987-2019, 'G.484' was evaluated for rooting ability (fair), lack of spine production (clean), and low root brittleness in a layering bed (stool bed). In 1993-96, apple rootstock 'G.484' was planted in a finished tree nursery to make evaluation trees. Several trees grafted with the scion variety *Malus domestica* 'Mutsu' (Not patented) were planted in a first test orchard in an apple farm (Geneva, N.Y.). In 2002, several replications of this rootstock grafted with the scion variety *Malus domestica* 'Golden Delicious' (Not patented) were planted in a second test orchard that measured dwarfing, cumulative yield (good), yield efficiency (medium-high), suckering (low-medium) and resistance to fire blight (100% survival). This rootstock performed well (top 20% of many rootstocks tested) in these orchard trials and during 2006-2019 more material was propagated by stool bed and finished tree nursery to be entered into new trials in Geneva, N.Y. which confirmed the productivity, stress tolerance and good propagation features of this rootstock.

II. Asexual Reproduction

Asexual reproduction of the 'G.484' apple rootstock has been achieved using the traditional method of clonally propagating apple rootstocks. In particular, the original seedling of the 'G.484' apple rootstock was planted in a field (Geneva, N.Y.) and allowed to develop into a "mother plant." The 'G.484' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants planted in a farm in Geneva, N.Y. In addition to conventional layering, the 'G.484' apple rootstock variety has been asexually reproduced by root cuttings, by budding and grafting onto seedling and clonal rootstocks, and by in vitro culture.

III. Stability

Observations of trees from these propagations indicate that all trees have proven true to type and identical in all appearances to the original tree through successive generations of asexual reproduction.

IV. Comparisons

The seed parent *Malus domestica* hybrid '722506-004' was a semi-vigorous breeding line, i.e., trees grown on this rootstock are 60 to 85 percent the size of a standard self-rooted seedling apple tree. '722506-004' displayed medium 'early bearing' trait which is to induce precocity to the scion (i.e., the ability to induce early reproductive development on grafted scions) and displayed moderate yield efficiency (i.e., the ability to produce many apples per square cm of trunk). '722506-004' produced few spines in stool bed clonal propagation, it was winter hardy, and susceptible to fire blight (*Erwinia amylovora*).

The pollen parent *Malus robusta* hybrid '74R5M9-823' was a semi-dwarfing rootstock, i.e. trees on this rootstock grow 40-70% the size of a standard self-rooted apple tree. '74R5M9-823' induced a medium level of 'early bearing' (precocity) to the scion and was yield efficient. Juvenile plants and young stool propagules of '74R5M9-823' produce medium spines. '74R5M9-823' was resistant to fire blight and to the woolly apple aphid.

The 'G.484' apple rootstock of the present invention combines the qualities of the parents such that some of the qualities are enhanced and distinguished from its parental plants (i.e., '722506-004' and '74R5M9-823'). For example, 'G.484' confers a level of dwarfing to grafted scions that is 30-45% of seedling which is more dwarfing than either parent. Furthermore, 'G.484' is resistant to certain strains of fire blight whereas the seed parent '722506-004' was not. 'G.484' has displayed excellent 'early bearing' or precocity properties that surpassed either of its parents. It is impossible to reproduce a rootstock exactly as 'G.484' as its parents were un-released breeding lines that have been eliminated from the breeding program and destroyed. 'G.484' is in the same vigor inducing class as industry standard 'M.26' (Not patented).

When compared to its pollen parent '74R5M9-823' this apple rootstock is similar because it is resistant to certain strains of fire blight, and the woolly apple aphid (*Eriosoma lanigerum*), but it is different because it produces less spines (sylleptic small branches) at the base of clonally propagated stool bed shoots.

As mentioned earlier, 'G.484' is most similar to 'Mailing 26' ('M.26'; Not patented) in terms of dwarfing (vigor) class and productivity. Differently than 'M.26', 'G.484' is resistant to several strains of fire blight and wooly apple aphid and has displayed significant tolerance to the replant disease complex.

BRIEF DESCRIPTION OF THE DRAWINGS

New apple tree rootstock 'G.484' is illustrated by the accompanying photographs. The ages of the trees depicted in the photographs are noted below. The colors shown are as true as can be reasonably obtained by conventional photographic procedures.

DETAILED BOTANICAL DESCRIPTION

Figure 1:
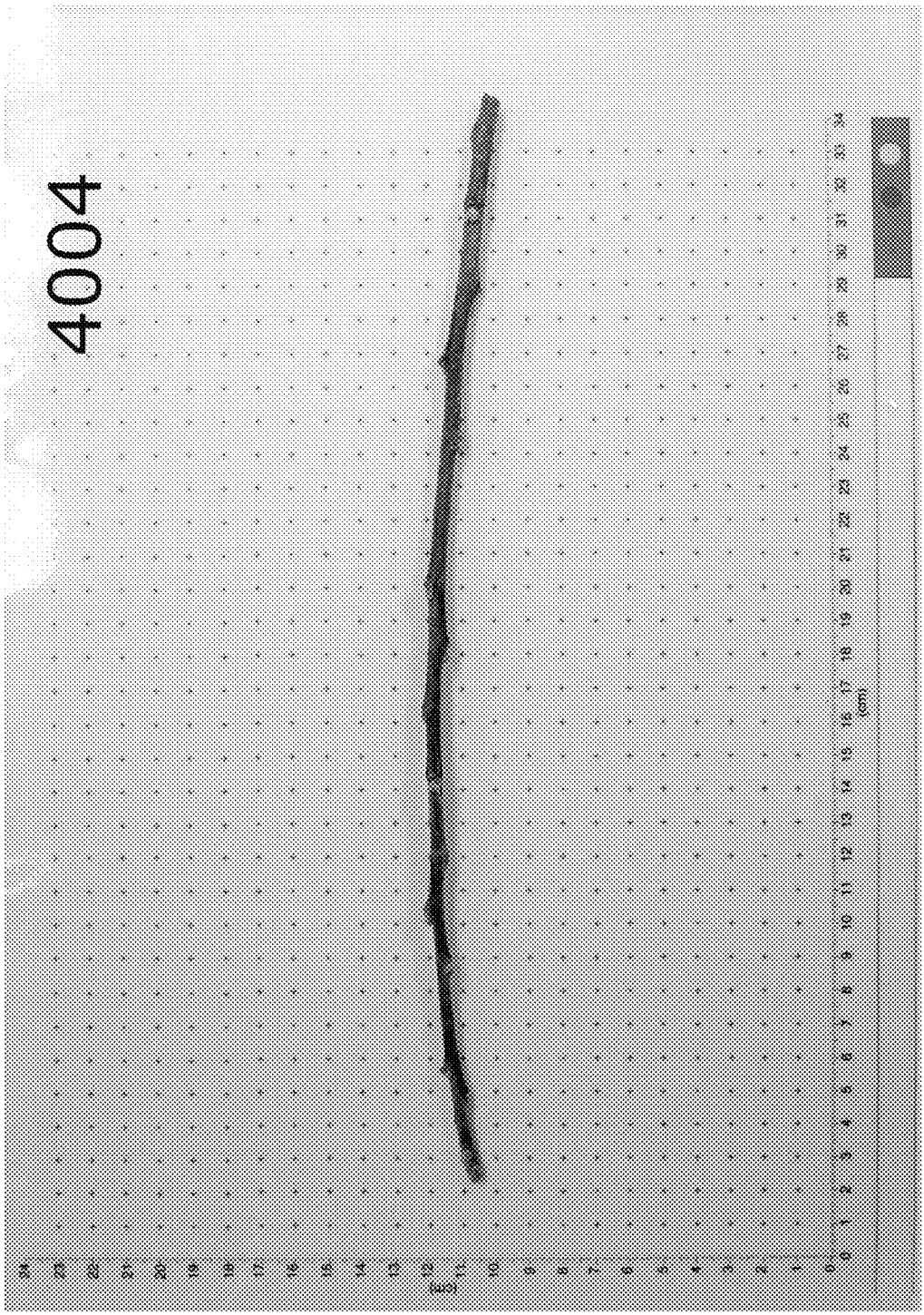
FIG. 1 shows a one year dormant shoot (including buds and bark).
Figure 2:
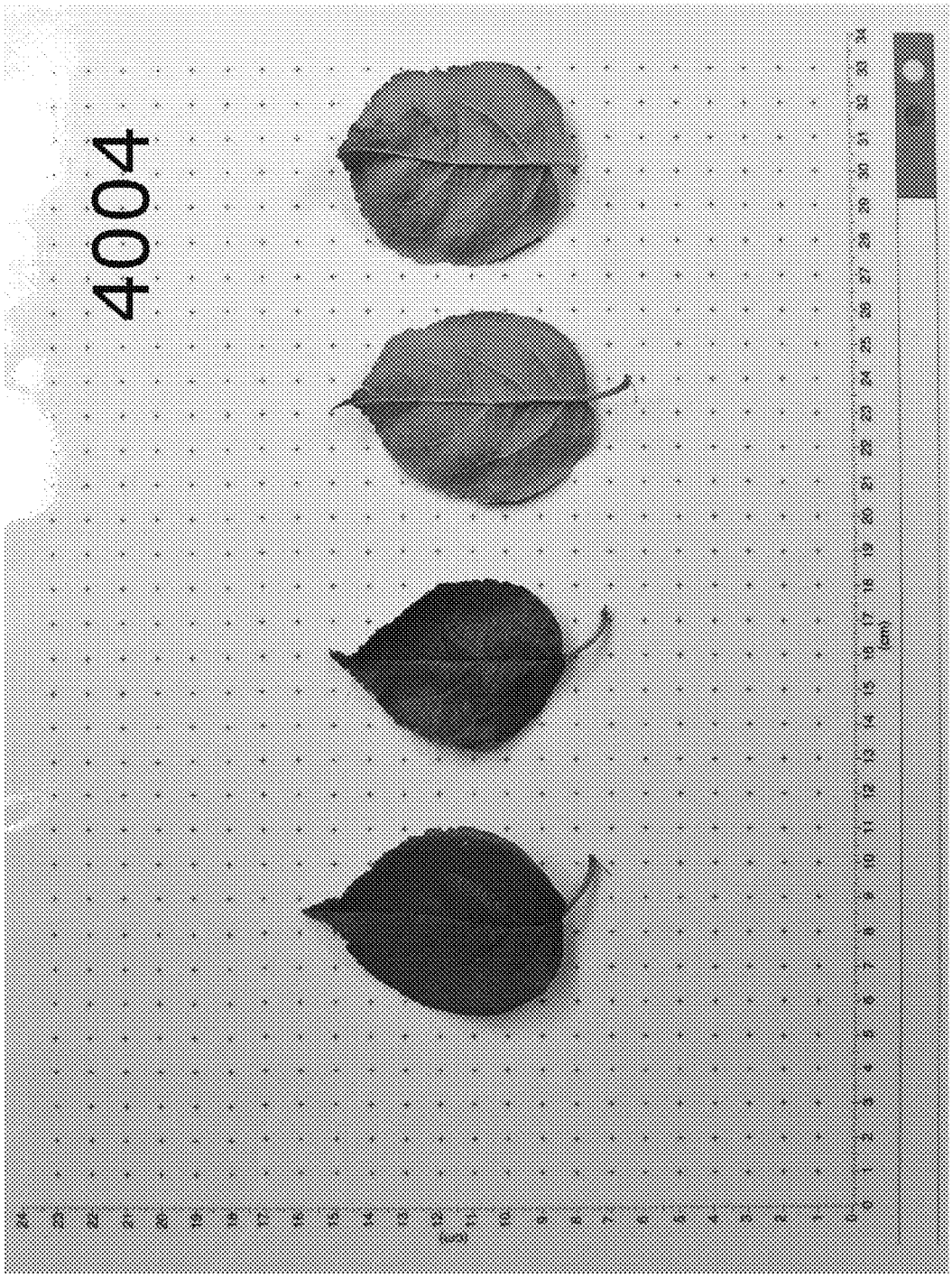
FIG. 2 shows adaxial (upper) and abaxial (lower) laminae of leaves.
Figure 3:
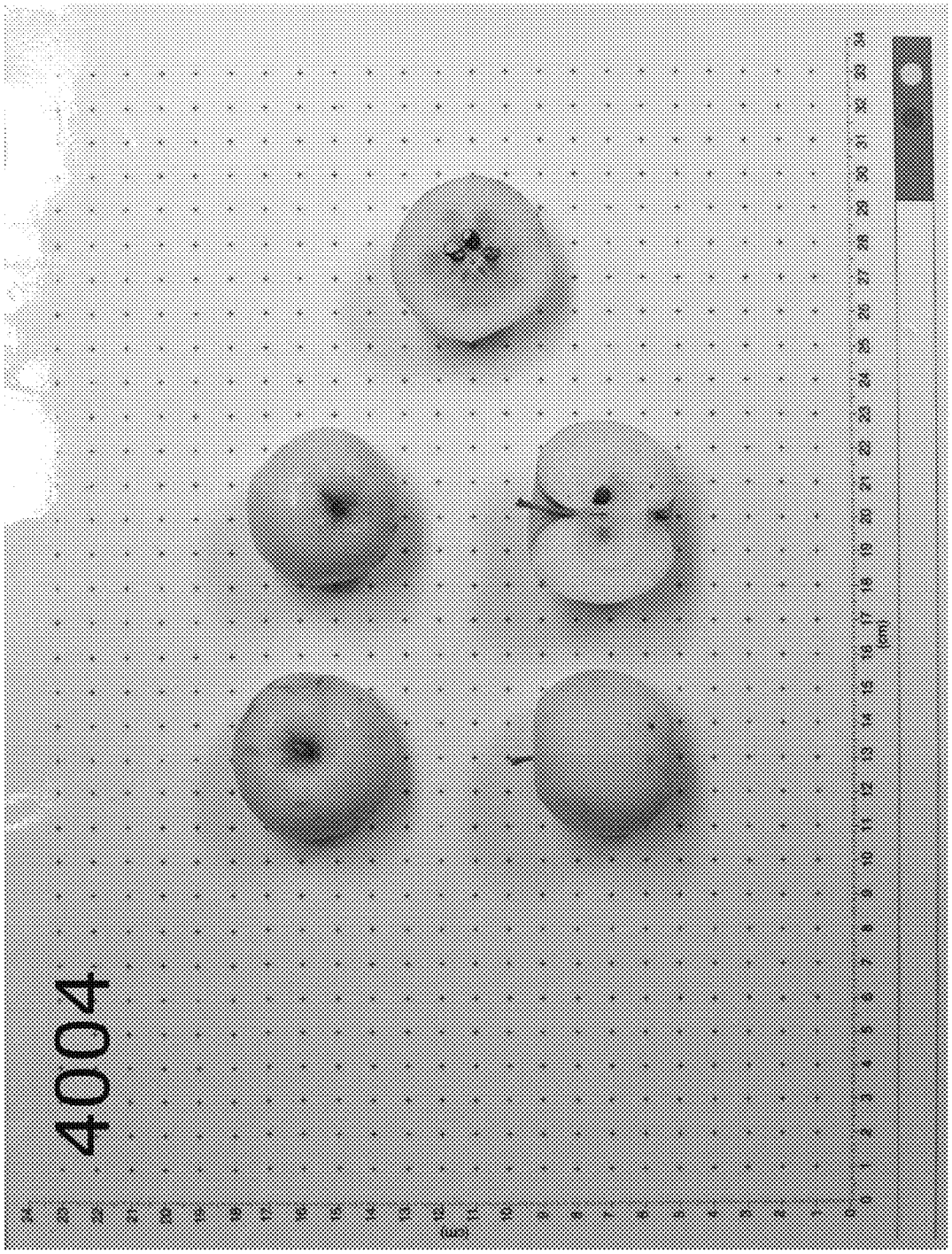
FIG. 3 shows fully mature fruit (interior and exterior).
Figure 4:
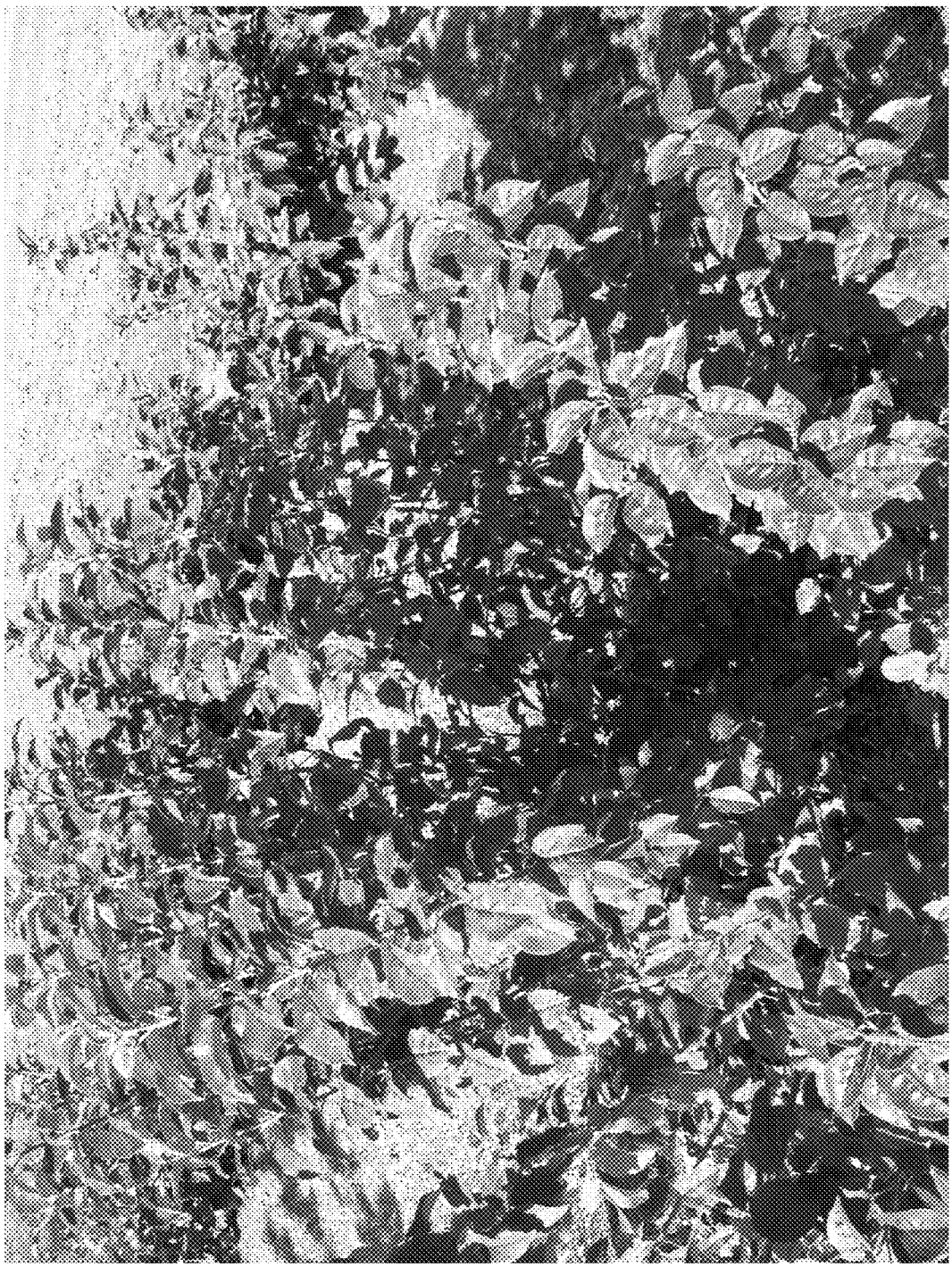
FIG. 4 shows a fully developed stool bed with leaves and shoots.
Figure 5:
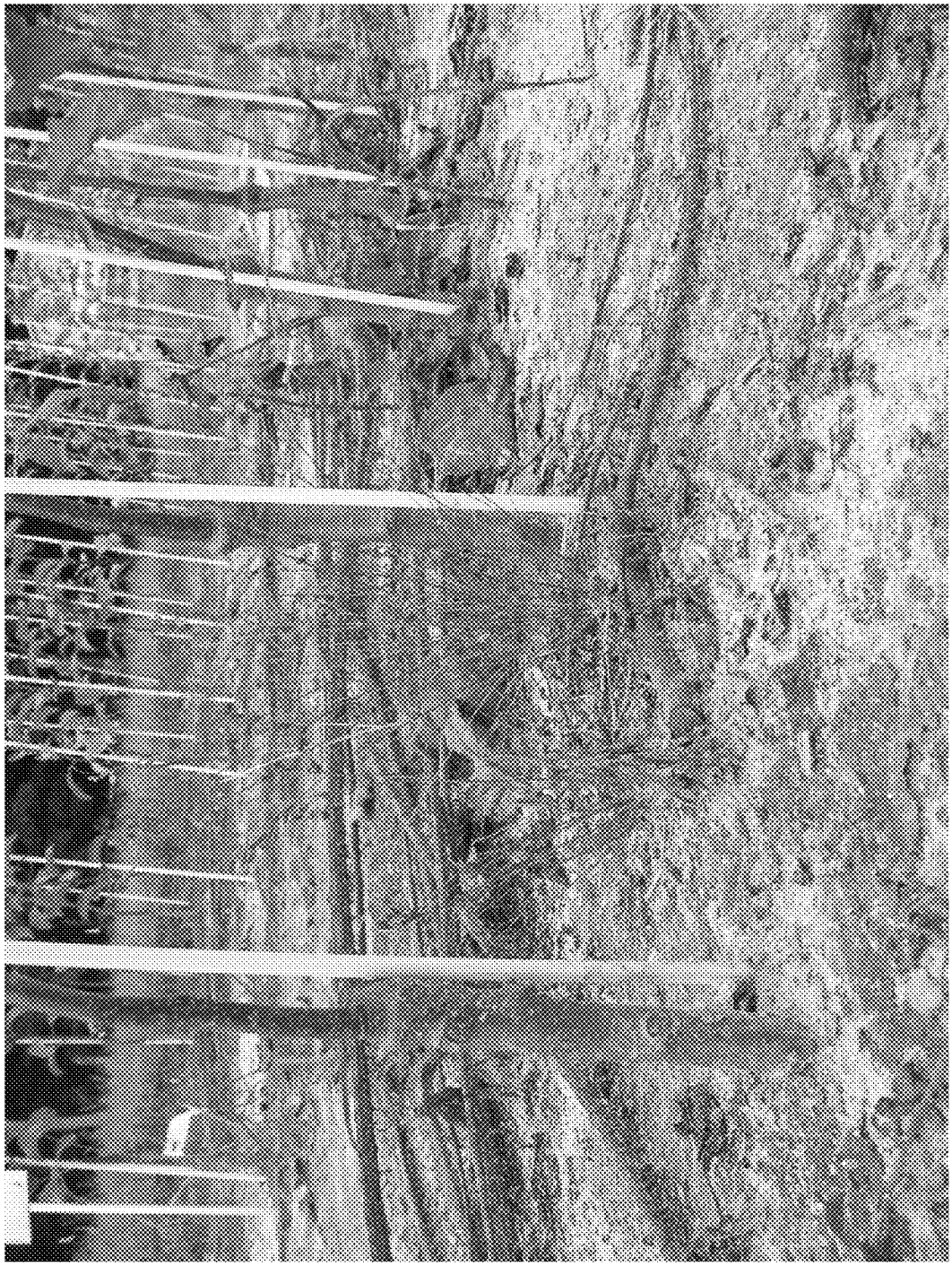
FIG. 5 shows graft unions on finished trees.
Figure 6:
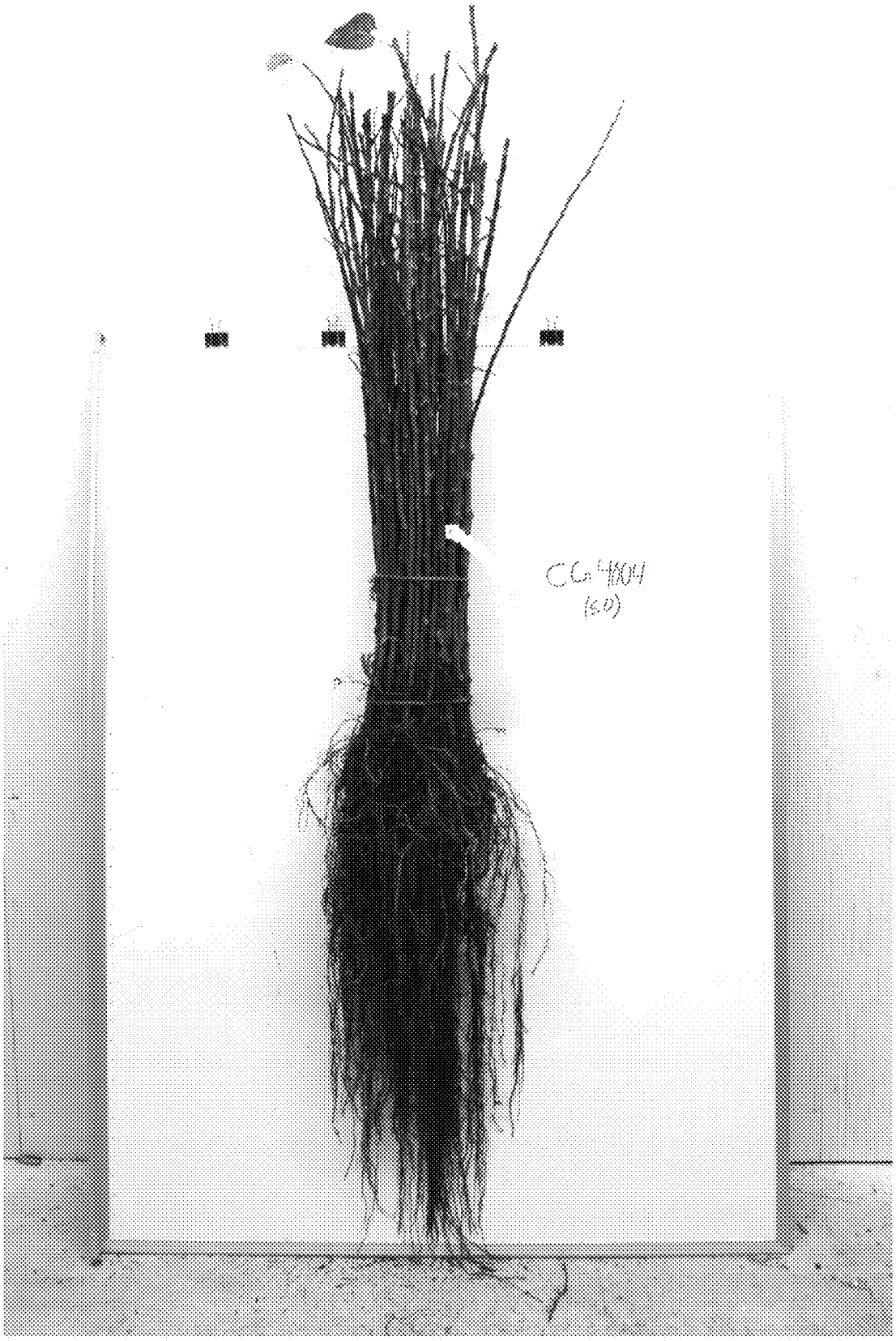
FIG. 6 shows a bundle of rooted rootstock liners.
Figure 7:
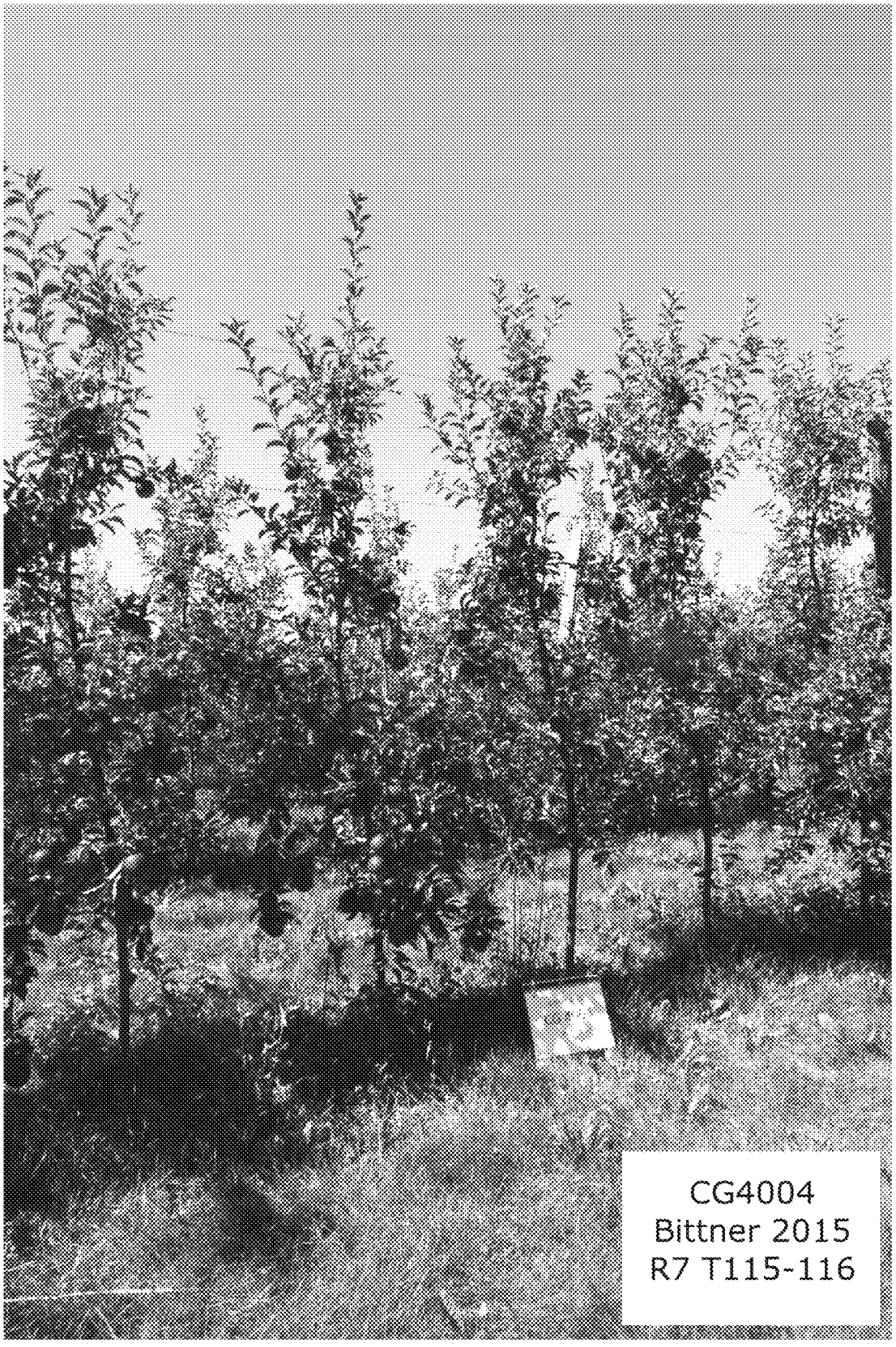
FIG. 7 shows 4-year-old trees in organic production.

The following description of apple tree rootstock 'G.484' contains references to color names taken from The Royal Horticultural Society Colour Chart (R.H.S.), 2001 edition. Botanical descriptions follow the Manual of Cultivated Plants (Bailey, 1949).

Tree:

*Habit*.—A self-rooted tree of 'G.484' is a shrub typically standing about 2-2.5 meters tall by about 2 meters wide when 7 years old. While it can be trained to a single dominant trunk, the persistent production of some root-borne suckers (i.e., new shoots emerging from below ground) means that it can evolve into a multi-trunk shrub. Liners planted in the nursery stop apical growth mid-season.

*Productivity*.—In an intermediate field trial performed in an apple orchard Geneva, N.Y., the 'G.484' rootstock received the cultivar 'Fuji' (*Malus domestica*; Not patented) as the scion and was compared to the *Malus domestica* check rootstocks 'M.9 EMLA' (Not patented), 'M.26' (Not patented) and 'M.7' (Not patented). 'G.484' displayed similar or higher cumulative production and similar yield efficiency (kg yield/$cm^2$ trunk cross sectional area) to all the check rootstocks.

*Precocity*.—Scion cultivars budded on 'G.484' exhibit the same precocity as those budded on 'M.26'.

*Fertility* (*fecundity*).—The 'G.484' plant produces flowers and fruits regularly.

Dormant shoots (buds and bark):

*Dormant mature shoots*.—Color: Greyed-Red (RHS 179A) where exposed to full sunlight grading to Yellow-Green (RHS 152A) with diminished light exposure. Texture: Pubescence which gradually disappears in older tissues. Size: 35-60 cm long; generally devoid of spines. Diameter: One year shoots can be 1.2 cm at the base and 0.8 cm at the apex, varying depending on placement of shoots in the plant.

*Axillary buds*.—Size: 4-6 mm long and 4 mm wide with evident pubescence. Shape: Obtuse, sessile, somewhat protruding. Texture: Evident pubescence.

*Bark on three-year-old shoots*.—Color: Greyed-Orange (RHS 172A to 172B). Lenticels: Color: Greyed-Orange (RHS 163B). Size: 0.3-0.4 mm in diameter. Quantity: 3-4 lenticels per $cm^2$.

Leaves:

*Mature leaves*.—Leaf arrangement: Alternate. Shape: Simple, flat, ovate. Size: Length: 80 mm. Width: 55 mm at the widest point. Laminae: Somewhat flat. Apex: Somewhat acuminate. Base: Nearly symmetrical rounded. Margin: Serrated, with about 3 serrations per cm. Upper surface: Color: Green (RHS 143A to 143B). Texture: Glabrous and translucent. Lower surface: Color: Yellow-Green (RHS 152D). Texture: Somewhat pubescent. Venation: Netted. Venation color: Gradation of Yellow-Green (RHS 153A) to shades of Greyed-Red (RHS 179A). Leaf poise: 25°-35° from the shoot, depending on shoot orientation. Stipules: Length: 6 mm. Width: 2 mm. Color: Green (RHS 143A to 143B) with some Greyed-Red (RHS 179A) at the base. Petioles: Diameter: 3 mm. Length: 15 mm. Texture: Somewhat pubescent. Color: Gradation of Yellow-Green (RHS 153A) to shades of Greyed-Red (RHS 179A) at the base attached to the stem.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot. Pubescence color: Greyed-White (RHS 156D). Color of scales beneath pubescence: Grey-Brown (RHS N 199B) to Greyed-Green (RHS N 189A), depending on exposure to sun. Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Pedicel*.—Length: 15 mm. Diameter: 2 mm. Texture: Somewhat pubescent. Color: Yellow-Green (RHS 151A).

*Petals*.—Size: Length: 25 mm. Width: 18 mm. Shape: Spatulate. Apex: Obtuse. Margin: Smooth. Texture: Smooth. Arrangement: Intermediate. Color: Closed petals: Red (RHS 54A). Opening petals: Flowers change color (intensity) as they open. Petals on the same flower will transition from Red to White with some red striations as they open and fully expand. Open petals: White (RHS 155D) with Red (RHS 54A) striations in some of the petals.

*Reproductive organs*.—Pistils: Length: 6 mm. Color: Yellow-white (RHS 145B). Stamens: Length: 4 mm. Color: White (RHS 155D). Anther color: Yellow-Brown (RHS 167D).

Fruit:

*Mature fruit*.—Size: Height: 40-45 mm. Diameter: 45-50 mm. Shape: Obloid. Color: Yellow-Orange (RHS 17C). Sepals: Persisting on an inset calyx. Flesh: Taste: Astringent (not meant for consumption). Color: Yellow-Orange (RHS 18A). Seed: Texture: Glabrous, smooth. Color: Greyed-Red (RHS 179A), translucent. Shape: Tear drop shape. Size: Length: 2-4 mm. Diameter: 3 mm at the widest point. Number: Generally five seed per fruit.

Disease resistance: As described above, the 'G.484' rootstock of the present invention exhibits resistance to fire blight. The percent lesion measured after inoculation of potted liners in the greenhouse using four different strains of *E. amylovora* was negligible for two of the strains and moderate for the other two, indicating a specific resistance to the bacterium. The 'G.484' rootstock, having survived the inoculation with crown and root rot, is also considered resistant to crown and root rots caused by *Phytophthora cactorum*. 'G.484' has displayed tolerance to the replant disease complex.

What is claimed is:

1. A new and distinct variety of apple tree named 'G.484' as herein described and illustrated.

* * * * *